US011467152B2

(12) United States Patent
Fenstermaker et al.

(10) Patent No.: US 11,467,152 B2
(45) Date of Patent: Oct. 11, 2022

(54) CIRCULATING SURVIVIN-POSITIVE EXOSOMES

(71) Applicant: Health Research, Inc., Buffalo, NY (US)

(72) Inventors: Robert A. Fenstermaker, Amherst, NY (US); Michael J. Ciesielski, Orchard Park, NY (US)

(73) Assignee: Health Research, Inc., Buffalo, NY (US)

( * ) Notice: Subject to any disclaimer, the term of this patent is extended or adjusted under 35 U.S.C. 154(b) by 676 days.

(21) Appl. No.: 16/470,197

(22) PCT Filed: Dec. 18, 2017

(86) PCT No.: PCT/US2017/067077
§ 371 (c)(1),
(2) Date: Jun. 14, 2019

(87) PCT Pub. No.: WO2018/112469
PCT Pub. Date: Jun. 21, 2018

(65) Prior Publication Data
US 2019/0331667 A1    Oct. 31, 2019

Related U.S. Application Data

(60) Provisional application No. 62/435,368, filed on Dec. 16, 2016.

(51) Int. Cl.
*G01N 33/50* (2006.01)
*A61K 39/00* (2006.01)
*A61K 9/127* (2006.01)

(52) U.S. Cl.
CPC ......... *G01N 33/5076* (2013.01); *A61K 9/127* (2013.01); *A61K 39/00115* (2018.08); *G01N 33/502* (2013.01); *G01N 2800/52* (2013.01); *G01N 2800/54* (2013.01); *G01N 2800/7028* (2013.01)

(58) Field of Classification Search
CPC .................................................. G01N 33/5076
USPC ........................................................ 435/7.23
See application file for complete search history.

(56) References Cited

U.S. PATENT DOCUMENTS

2014/0228233 A1* 8/2014 Pawlowski ...... G01N 33/57484
435/7.92
2015/0301058 A1   10/2015 Schettini et al.

OTHER PUBLICATIONS

Muller, L., et al., Exosomes isolated from plasma of glioma patients enrolled in a vaccination trial reflect antitumor immune activity and might predict survival, Oncoimmunology, Jun. 2015, vol. 4, No. 6, e1008347, 8 pages.
Fenstermaker, R.A., et al., Clinical study of a survivin long peptide vaccine (SurVaxM) in patients with recurrent malignant glioma, Cancer Immunol Immunother, Aug. 30, 2016, vol. 65, pp. 1339-1352.
Ciesielski, M.J., et al., Circulating CD9-GFAP-survivin exosomes during active specific immunotheraphy, a potential biomarker for glioma, Proceedings: AACR Annual Meeting, Jul. 2017, vol. 77, No. 13, 4 pages.

\* cited by examiner

*Primary Examiner* — Sean E Aeder
(74) *Attorney, Agent, or Firm* — Hodgson Russ LLP

(57) ABSTRACT

Provided is a method for evaluating the progression of glioma in an individual comprising monitoring the levels of circulating exosomes that are positive for survivin and a glial marker (such as glial fibrillary acidic protein). An increase in the level of such exosomes is indicative of poor prognosis. Levels of circulating exosomes that are positive for survivin and glial marker can also be used for evaluating the efficacy of a therapy for glioma in an individual, and modifying the therapy or introducing additional therapy if levels of such exosomes are found to be increasing.

12 Claims, 11 Drawing Sheets

Specification includes a Sequence Listing.

Table 1.

| Patient | Age | Sex | Tumor type[1] | IDH-1 (R132H) | Disease Burden[2] | Survivin Positive Cells in Tumor (%) | Doses of Vaccine | PFS (weeks) |
|---|---|---|---|---|---|---|---|---|
| 1 | 38 | M | G | + | + | 22% | 4 + 14 | 173.7 |
| 2 | 58 | M | G | + | + | 1% | 4 + 2 | 88.0 |
| 3 | 57 | M | A | + | + | 2% | 4 + 1 | 96.4 |
| 4 | 45 | F | G | + | +++ | 10% | 4 | 8.0 |
| 5 | 52 | F | G | - | + | 7% | 4 | 8.6 |
| 6 | 48 | F | G | - | ++ | 8% | 4 | 10.4 |
| 7 | 61 | M | G | + | + | 15% | 4 | 25.1 |
| 8 | 54 | M | G | + | + | 4% | 4 | 9.4 |

Figure 6

Table 2.

| Patient | GFAP+ (% Total CD9+ Exosomes) | | | | |
|---|---|---|---|---|---|
| | Baseline | 8 Weeks | % change | Extended | % change |
| 1 | 23.7 | 25.9 | 9% | 33.1 | 40% |
| 5 | 18.2 | 16.9 | -7% | 26.3 | 45% |
| 7 | 22.9 | 20.5 | -10% | 18.7 | -18% |
| 2 | 25.0 | 30.3 | 21% | | |
| 3 | 19.8 | 19.4 | -2% | | |
| 6 | 24.9 | 19.1 | -23% | | |
| 8 | 21.0 | 17.8 | -15% | 16.0 | -24% |
| 9 | 27.1 | 26.5 | -2% | | |
| C1 | 2.9 | | | | |
| C2 | 3.2 | | | | |
| C3 | 2.7 | | | | |

| Patient | GFAP+ (% Total CD9+ Exosomes) | | | | |
|---|---|---|---|---|---|
| | Baseline | 8 Weeks | % change | Extended | % change |
| 1 | 23.7 | 25.9 | 9% | 33.1 | 40% |
| 5 | 18.2 | 16.9 | -7% | 26.3 | 45% |
| 7 | 22.9 | 20.5 | -10% | 18.7 | -18% |
| 2 | 25.0 | 30.3 | 21% | | |
| 3 | 19.8 | 19.4 | -2% | | |
| 6 | 24.9 | 19.1 | -23% | | |
| 8 | 21.0 | 17.8 | -15% | 16.0 | -24% |
| 9 | 27.1 | 26.5 | -2% | | |
| C1 | 2.9 | | | | |
| C2 | 3.2 | | | | |
| C3 | 2.7 | | | | |

Figure 7

Table 2. (continued)

| Patient | Survivin+ (% Total CD9+ Exosomes) | | | | |
|---|---|---|---|---|---|
| | Baseline | 8 Weeks | % change | Extended | % change |
| 1 | 12.1 | 0.4 | -97% | 0.9 | -93% |
| 5 | 35.0 | 17.1 | -51% | 11.4 | -67% |
| 7 | 0.8 | 1.2 | 53% | 0.3 | -63% |
| | 5.1 | 2.0 | -61% | | |
| 3 | 1.6 | 14.1 | 781% | | |
| | 6.7 | 31.7 | 373% | | |
| | 6.3 | 27.5 | 340% | 46.5 | 644% |
| 9 | 5.3 | 2.3 | -57% | | |
| C1 | 0.1 | | | | |
| C2 | 0.0 | | | | |
| C3 | 1.2 | | | | |

| Patient | Survivin+ (% Total CD9+ Exosomes) | | | | |
|---|---|---|---|---|---|
| | Baseline | 8 Weeks | % change | Extended | % change |
| 1 | 12.1 | 0.4 | -97% | 0.9 | -93% |
| 5 | 35.0 | 17.1 | -51% | 11.4 | -67% |
| 7 | 0.8 | 1.2 | 53% | 0.3 | -63% |
| | 5.1 | 2.0 | -61% | | |
| 3 | 1.6 | 14.1 | 781% | | |
| | 6.7 | 31.7 | 373% | | |
| | 6.3 | 27.5 | 340% | 46.5 | 644% |
| 9 | 5.3 | 2.3 | -57% | | |
| C1 | 0.1 | | | | |
| C2 | 0.0 | | | | |
| C3 | 1.2 | | | | |

Figure 7 (continued)

Table 2. (continued)

| Patient | Survivin+/GFAP+ (% Total CD9+ Exosomes) | | | | |
|---|---|---|---|---|---|
| | Baseline | 8 Weeks | % change | Extended | % change |
| | 10.4 | 0.3 | -98% | 0.6 | -94% |
| | 27.2 | 11.5 | -58% | 9.0 | -67% |
| | 0.6 | 0.4 | -31% | 0.2 | -65% |
| | 3.2 | 1.2 | -63% | | |
| | 0.6 | 9.7 | 1417% | | |
| | 4.4 | 21.6 | 393% | | |
| | 4.4 | 19.8 | 349% | 37.6 | 753% |
| | 3.8 | 1.4 | -63% | | |
| | 0.0 | | | | |
| | 0.0 | | | | |
| | 0.1 | | | | |

| Patient | Survivin+/GFAP+ (% Total CD9+ Exosomes) | | | | |
|---|---|---|---|---|---|
| | Baseline | 8 Weeks | % change | Extended | % change |
| | 10.4 | 0.3 | -98% | 0.6 | -94% |
| | 27.2 | 11.5 | -58% | 9.0 | -67% |
| | 0.6 | 0.4 | -31% | 0.2 | -65% |
| | 3.2 | 1.2 | -63% | | |
| | 0.6 | 9.7 | 1417% | | |
| | 4.4 | 21.6 | 393% | | |
| | 4.4 | 19.8 | 349% | 37.6 | 753% |
| | 3.8 | 1.4 | -63% | | |
| | 0.0 | | | | |
| | 0.0 | | | | |
| | 0.1 | | | | |

Figure 7 (continued)

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: modified survivin peptide from human

<400> SEQUENCE: 1

Asp Leu Ala Gln Met Phe Phe Cys Phe Lys Glu Leu Glu Gly Trp
1               5                   10                  15
```

CIRCULATING SURVIVIN-POSITIVE EXOSOMES

CROSS-REFERENCE TO RELATED APPLICATIONS

This application claims priority to U.S. Provisional patent application No. 62/435,368, filed on Dec. 16, 2016, the disclosure of which is incorporated herein by references.

BACKGROUND OF THE DISCLOSURE

A persistent challenge in the treatment of gliomas is the ability to monitor progress and predict outcomes using non-invasive or minimally invasive techniques. Accurate monitoring of disease progression would allow evaluation of effectiveness of ongoing therapeutic approaches and rapid adjustment of treatment regimens if the current treatment is not producing the expected results.

SUMMARY OF THE DISCLOSURE

The inhibitor of apoptosis protein (IAP) survivin (SVN) promotes cancer cell proliferation and resistance to chemotherapy and its expression is associated with a poor prognosis. Survivin is expressed in many cancer types including malignant gliomas and is a potential target for active immunotherapy. This disclosure is based on our evaluation of circulating exosomes isolated from the serum of malignant glioma patients enrolled in a phase I clinical trial of an anti-survivin vaccine (SurVaxM). Exosomes are endosome-derived microvesicles ranging in size from 30-100 nm. Glioma cells release exosomes in culture and into the extracellular matrix in vivo. These microvesicular bodies transport an array of proteins, lipids, and RNA species, suggesting a potential mechanism for cell-cell communication. We found that serum from glioma patients contained CD9+ exosomes with both survivin and glial fibrillary acidic protein (GFAP) on their surface, as measured by enhanced imaging and cytometry technology. Survivin and GFAP were evaluated independently and together as markers on CD9+ exosomes. Patients with longer time to tumor progression (TTP) exhibited a decrease in circulating CD9+/GFAP+/SVN+ exosomes following survivin vaccination, whereas, those with early tumor progression had either a transient decrease, or an increase in GFAP+/SVN+ exosomes despite vaccination. Non-cancer healthy controls did not have detectable CD9+/GFAP+/SVN+ exosomes in their sera. This study demonstrates that malignant glioma patients have CD9+/GFAP+/SVN+ exosomes in their peripheral circulation and that reductions in their numbers following anti-survivin therapy might be associated with better disease control; whereas, increased numbers of these specific exosomes are associated with tumor progression.

Based on our findings, this disclosure provides methods for evaluating the progression of cancer, such as glioma, in an individual. For example, this disclosure provides a method for diagnosis and/or prognosis of individuals afflicted with cancer, such as, for example, glioma. The method comprises obtaining a biological fluid from an individual who is in need of diagnosis or prognosis or monitoring, obtaining a purified or enriched population of exosomes from the biological sample, labeling the exosomes with detectors of specific markers, subjecting the exosome population to enhanced imaging and flow cytometry to determine if survivin positive exosomes that also exhibit a glial marker are present. The presence of such exosomes is used to draw inferences regarding the status or progression of glioma in the individuals. Progression of therapeutic interventions, including immunotherapeutic intervention, can be followed. Therapy can be adjusted based on the levels of the circulating exosomes that are positive for SVN and the cancer marker (such as the glial marker).

In one aspect, this disclosure provides a method of evaluating the efficacy of a therapy in an individual who is being treated for a cancer, such as glioma. The method comprises i) determining the level of CD9+/GFAP+/SVN+ exosomes (such as by high resolution imaging and flow cytometry) in a biological fluid such as blood (or serum or plasma), ii) determining whether the level of the CD9+/GFAP+/SVN+ exosomes is at or below a reference value, with such determination indicating that the therapy is efficacious; and iii) continuing with the current therapeutic regimen in an individual having a level of CD9+/GFAP+/SVN+ exosomes at or below the reference value; and discontinuing or modifying the current therapy in an individual having a level of CD9+/GFAP+/SVN+ exosomes that is above the reference value. The term CD9+/GFAP+/SVN+ exosomes means the exosomes exhibit the presence of CD9, GFAP and SVN.

The reference value can be the level of CD9+/GFAP+/SVN+ exosomes in the blood obtained from the individual prior to the treatment or at any selected time point prior to, during, or after the completion of the treatment. For example, if an individual is subjected a surgical removal of the glioma, a reference value can be obtained prior to or just after removal of the glioma. If surgery is followed (or preceded) by radiation or chemotherapy, again, a reference value can be obtained prior to, during or after completion of any or all of these modalities. If one or more of surgery, radiation or chemotherapy is to be followed by administration of a vaccine (such as a survivin peptide), a reference value can be obtained just prior to, or shortly after the administration of the vaccine. The reference value may also be the level obtained from one or more individual who have not been diagnosed with glioma.

In one aspect, this disclosure provides a method for treatment of an individual who has been diagnosed with glioma. The method comprises surgical resection of the glioma, followed by administration of an immunogenic vaccine, wherein the vaccine comprises a modified survivin peptide (such as having SEQ ID NO:1). At various times following the surgical resection (including after administration of the vaccine), the levels of circulating CD9+/GFAP+/SVN+ exosomes can be evaluated. Reference values can be obtained before and shortly after surgery. If the levels of CD9+/GFAP+/SVN+ exosomes are found to be increasing after administration of the vaccine, then the vaccine is deemed to be inefficacious in the individual and the individual can be subjected to further treatments such as one or more of surgical, radiation or chemotherapeutic treatments. However, if the levels of CD9+/GFAP+/SVN+ are not found to increase after administration of the vaccine, then the vaccine is considered to be efficacious in the individual and any ongoing treatment does not need to be modified and can be continued. Thus, modification of the ongoing surgical, radiation or chemotherapeutic intervention can be avoided or postponed.

BRIEF DESCRIPTION OF THE FIGURES

FIG. 6. (Also referred to herein as Table 1) is a representation of patient characteristics[1] G, glioblastoma; A, anaplastic glioma; [2]Disease burden measured on MRI at first dosing: (−) no measureable contrast enhancement (C.E.); (+), measureable C.E.<1 cm$^3$; (++), >1 cm$^3$ but ≤5 cm$^3$ C.E.; (+++), >5 cm$^3$ C.E.; PFS: progression-free survival.

FIG. 7. (Also referred to herein as Table 2) is a representation of exosomes in Late Progression (LP), Early Progression (EP), and Controls.

DESCRIPTION OF THE DISCLOSURE

Figure 1:
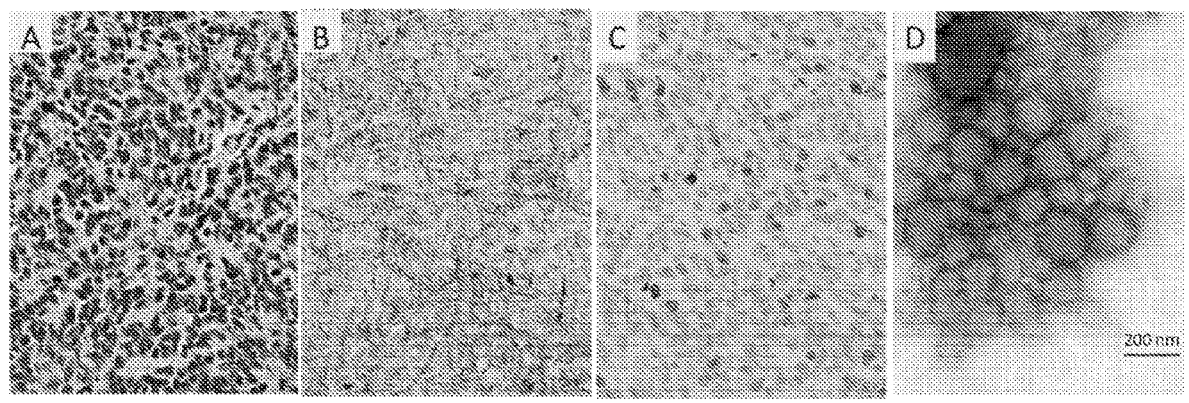
FIG. 1. Immunohistochemistry and exosome morphology. Representative images of: A) hematoxylin and eosin stain of recurrent glioblastoma from patient #1 displaying small cell features and immunostain of sections from the same tumor for B) GFAP, and C) survivin. D) Electron microscopic image of exosomes isolated from the serum of patient #2 at baseline. The image was captured at 50,000× (scale bar indicates 200 nm).

Survivin (BIRC5) is an inhibitor of apoptosis protein (IAP) that is over-expressed in a large number of tumor types, including malignant gliomas. High expression of survivin in gliomas and other cancers is associated with a poor prognosis and refractoriness to chemotherapy. Our group found survivin to be immunologically targetable using a peptide mimic encompassing amino acids 53-67 of the human protein. Injection of DLAQMFFCFKELEGW–keyhole limpet hemocyanin (KLH) (SurVaxM) (SVN53-67/M57-KLH) (SEQ ID NO:1) into glioma-bearing mice resulted in significantly longer survival and enhanced tumor-directed CTL responses (Ciesielski 2010). More recently, the completed Phase I clinical trial demonstrated the immunogenicity of SurVaxM in glioma patients who had failed to respond to standard therapies.

In the current study, we examined serum-derived exosomes from glioblastoma patients who had undergone survivin-targeted active specific immunotherapy in the SurVaxM Phase I clinical trial. Our findings demonstrate that patients with malignant gliomas express a unique population of circulating exosomes containing both survivin and the CNS/glioma-marker protein GFAP (Glial fibrillary acidic protein). In this disclosure, we provide a method for obtaining and identifying this unique population of circulating exosomes that exhibit both survivin and a glial marker.

Whenever a range is described in this disclosure, all values within that range are also disclosed. The use of singular or "a" or "an" also includes a plurality of the articles or materials. For example, the term "an antibody" includes "antibodies".

In one aspect, this disclosure provides a method of monitoring the progression of a cancer by identifying the presence and/or numbers of circulating exosomes exhibiting markers specific for the particular cancer cell type and survivin. For example, this disclosure provides a method for monitoring the progression of glioma. The method comprises obtaining enriched populations of exosomes and determining if the exosomes exhibit survivin and a glioma specific marker (as compared to a reference value). An example of a glioma specific marker is GFAP. The method can also be used for determining the status and progression of lung cancer and other cancers as well as for monitoring therapeutic approaches. In those instances, tissue/tumor specific markers can be employed with survivin.

A biological sample can be obtained from an individual in need of monitoring the status. Examples of biological samples include blood, serum, plasma, saliva, sputum, urine, pleural fluid, ascites fluid, peritoneal fluid, cerebrospinal fluid, bronchoalveolar lavage fluid, tears, or fluid derived from in vitro tissue culture of patient tissues/tumor and combinations thereof. For example, the biological sample can be serum or plasma.

Exosomes may be isolated by a variety of methodologies, such as density gradient centrifugation, differential centrifugation, nanomembrane ultrafiltration, immunoabsorbent capture, affinity capture, size-exclusion chromatography, ultracentrifugation, and ultracentrifugation followed by size-exclusion chromatography, magnetic activated cell sorting, and the like. For example, if blood samples are used, serum can be obtained from the blood, and then the serum can be subjected to ultracentrifugation, such as 100,000×g or more for 10 to 120 mins to more. Another method involves use of polyethylene glycol (PEG) and then ultracentrifugation. Commercially available kits may be used, such as one available from Thermo-Fisher Scientific Inc. (Waltham, Mass.). The enriched exosomes can be suspended in suitable buffers for analysis.

Exosome populations are assessed for purity based upon expression of CD9 surface marker. To be included in this analysis the exosome are required to be CD9+. Additional tissue origin markers may be included to focus upon organ specific generation, such as GFAP for brain derived tumors. The exosome populations can be at least 90 or 95% pure for exosome as judged by electron microscopy for vehicles from 10 to 200 nm, which is consistent with the purity estimated from CD9+ staining. The enriched population may be 90, 91, 92, 93, 94, 95, 96, 97, 98, 99 or 100% pure for exosomes.

Suitable buffers include phosphate buffer, citrate buffer, glycine, tris(hydroxymethyl)aminomethane hydrochloride (TRIS), N-(2-hydroxyethyl)piperazine-N′-2-ethanesulfonic acid (HEPES), 3-(N-morpholino) propanesulfonic acid (MOPS), 2-(N-morpholino) ethanesulfonic acid (MES), N-tris[hydroxymethyl]methyl-2-aminoethanesulfonic acid (TES), N-[carboxymethyl]-2-aminoethanesulfonic acid (ACES), N-[2-acetamido]-2-iminodiacetic acid (ADA), N,N-bis[2-hydroxyethyl]-2-aminoethanesulfonic acid (BES), N-[2-hydroxyethyl]piperazine-N-[2-hydroxypropanesulfonic acid] (HEPPSO), N-tris[hydroxymethyl]methylglycine (TRICINE), N,N-bis[2-hydroxyethyl]glycine (BICINE), 4-(cyclohexylamino)-1-butanesulfonic acid (CABS), 3-(cyclohexylamino)-1-propanesulfonic acid (CAPS), 3-(cyclohexylamino-2-hydroxy-1-propanesulfonic acid (CAPSO), 2-(cyclohexylamino)ethanesulfonic acid (CHES), N-(2-hydroxyethyl)piperazine-N'-(3-propanesulfonic acid) (EPPS), piperazine-N,N'-bis(2-ethanesulfonic acid (PIPES), [(2-hydroxy-1,1-bis[hydroxymethyl]ethyl) amino]-1-propanesulfonic acid (TAPS), N-tris(hydroxymethyl)methyl-4-aminobutane sulfonic acid (TABS), 2-amino-2-methyl-1-propanol (AMP), 3-[(1,1-dimethyl-2-hydroxyethyl)amino]-2-hydroxypropanesulfonic acid (AMPSO), ethanolamine, 3-amino-1-propanesulfonic acid, and the like.

The exosomes can then be evaluated for the presence of relevant markers. To ensure the population is comprised of exosomes or predominantly exosomes, markers specific to exosomes can be evaluated. For example, the presence of one or more of tetraspanins (CD63, CD9 and CD81), heat shock proteins (HSP70) and proteins from the Rab family (e.g., Rab5), Tsg101 and Alix, can be determined. These markers are not known to be present in other vesicles of similar size. In one embodiment, the exosome marker is CD9.

In the case of exosomes from glioma patients, a suitable marker for glial origin is GFAP. Other glioma markers may include Aldehyde Dehydrogenase (ALDH1L1), Aldolase C, GDNF, GDNFR, Galectin-3, PTEN, Sox2, and Vimentin.

For evaluation of markers, one or more of the following can be determined: CD9, GFAP and survivin. For example, GFAP and survivin can be determined in enriched exosomes. In one embodiment, all three markers CD9, survivin and GFAP can be determined.

The presence of the makers can be determined by using detectably labeled (direct or indirect) specific binding partners for the markers. Such binding partners include specific ligands, receptors, antibodies (or antigen binding fragments thereof) or synthetic molecules that specifically recognize the markers. Examples for detecting CD9, GFAP and/or survivin are antibodies, which may be monoclonal or polyclonal, chimeric, humanized, single chain, nanobodies, or a fragment or variant of any of the foregoing that binds specifically to CD9, survivin or GFAP.

In the course of these studies, it was observed that the presence of CD9+/survivin/GFAP positive exosomes could not be detected using routine flow cytometry (which generally has a resolution of about 300 to 400 microns). It was only with the use of combination of high resolution imaging (which enhances the resolution to about 20 microns), with flow cytometry that the CD9/survivin/GFAP positive exosomes could be detected. An example of a high resolution imaging combined with flow cytometry is ImageStream®X and ImageStream®X Mark II Imaging Flow Cytometer (AMNIS/Millipore). The ImageStream® Imaging Flow Cytometer combines the speed, sensitivity, and phenotyping abilities of flow cytometry with the detailed imagery and functional insights of microscopy. This combination of high resolution imaging and flow cytometry enabled the detection of CD9/survivin/GFAP positive exosomes that we were not able to detect using either technique alone. With this instrument, we were able to obtain multiple high-resolution images of each particle directly in flow, including brightfield and darkfield (SSC), with sensitivity exceeding conventional flow cytometers. Therefore, in one embodiment, the evaluation of the presence of CD9/survivin/GFAP exosomes is carried out by high resolution imaging and flow cytometry.

While the method of the present disclosure can be used as a diagnostic tool for glioma on any individual, it is more useful for monitoring the status of progression of the disease in individuals who are being treated or who have had recurrence of the disease. Treatment options for gliomas generally involve surgery coupled with radiation and/or chemotherapy. An immunotherapy approach, such as the use of a vaccine, can also be used. Radiation and/or chemotherapy are generally instituted a few weeks after surgery. The present method can be carried out at any time after surgery. For example, it can be carried out after surgery as frequently as considered desirable by a physician. For example it can be carried out every day to every week (or another suitable frequency—which can vary). In one embodiment, testing for survivin positive exosomes can be carried out at a suitable time to obtain a reference value, and then determination can also be carried out 2-3 weeks after surgery. Determinations can be carried out during the time period that chemotherapy or radiation treatment regimens are being carried out, and/or determinations can be carried out after completion of the treatment regimens for as long as it is considered desirable.

The measured values of survivin and GFAP positive exosomes can be compared to reference values. A reference (or a predetermined value) can be an initial value (such as prior to surgery, or right after surgery or at any time point during treatment), or can be a value obtained from an individual or a population of individuals who do/does not have glioma.

An increased level of survivin and GFAP positive exosomes compared to a reference value is indicative of enhanced progression of the disease and poor prognosis. Increased levels of survivin and GFAP positive exosomes (e.g. CD9+/GFAP+/SVN+ exosomes) can serve as a marker of treatment efficacy. A patient displaying increased exosomes may be afforded an opportunity for different therapeutic decisions at an earlier time point than would be detected using current technology.

In one aspect, this disclosure provides a method of treatment of an individual who is afflicted with glioma. The method comprises surgical removal of glioma, measurement of CD9+/GFAP+/SVN+ exosomes after the surgical removal (reference value), administration of a composition comprising the peptide of SEQ ID NO:1, measurement of CD9+/GFAP+/SVN+ exosomes over a period of several weeks to months, determining if the levels of CD9+/GFAP+/SVN+ exosomes are increasing over the reference value, and subjecting the individual to additional treatment (further surgery, radiation, chemotherapy, or immune therapy) if the levels are increasing. If the levels are the same or decreasing compared to the reference value, then additional treatment or a change in treatment regimen is not be warranted.

In one embodiment, this disclosure provides a method for monitoring the presence of or progression of glioma in a subject comprising: (a) obtaining a biological sample from the subject; (b) obtaining an exosome rich fraction from the biological sample; (c) contacting the exosomes with detection agents for exosome marker, survivin, and glial marker; (d) subjecting the sample from (c) through an enhanced imaging/flow cytometry process; (e) comparing the value obtained in (d) with a reference value to determine if the level of exosome marker, survivin and glial marker positive exosomes in increased, wherein a determination of increased levels is indicative of a progression of glioma in the subject. The exosome marker can be CD9 and the glial marker can be glial fibrillary acidic protein. The individual subject may have undergone surgical removal of a glioma, or may have been exposed to radiation, chemotherapy, or immune therapy, or a combination of any two or more of these modalities. The reference value can be obtained from the same individual or a different individual or a group of individuals who are not afflicted with the particular type of cancer (e.g. glioma). The reference value can be determined when needed or can be obtained ahead of time, and can be a stored reference value.

In one aspect, this disclosure provides kits for evaluation of survivin and GFAP positive exosomes in individuals. The kits can contain one or more exosome specific antibodies either alone or in predetermined combinations, exosome isolation reagents and control exosome sizing particles. The kit may also contain labeled antibodies for detection of glial markers such as GFAP and labeled antibodies for detection of survivin.

Our study is the first to look at a specific combination of tumor-associated proteins (CD9, GFAP and survivin) expressed on GBM exosomes from patients being treated with an immunotherapeutic agent, SurVaxM. Increases in CD9+/GFAP+/SVN+ exosomes were found to be associated with a short time to relapse, implying that they may represent markers for tumor progression. The present methods can be used in monitoring of glioma progression via obtaining biopsy samples, including liquid biological samples such as blood, plasma, serum, cerebrospinal fluid etc., or other liquid biopsy samples. The present methods may be used for detection of disease-specific exosomes containing multiple markers in other malignancies.

The invention is further described through the following examples, which are intended to be illustrative, and not restrictive.

EXAMPLE 1

Methods

Study Overview

This clinical study (NCT01250470), from which blood samples were derived, was conducted in patients with survivin-positive malignant gliomas that had recurred or progressed following standard therapy. All patients had developed recurrent disease after at least: surgical resection, standard fractionated radiation therapy and one or more regimens of chemotherapy, including at least temozolomide. Vaccine characteristics and the results of this nonrandomized, single-institution, first-in-man clinical trial designed to assess a fixed dose anti-survivin vaccine regimen were recorded. Briefly, a regimen of SVN53-67/M57-KLH (500 µg) with Montanide ISA 51 and sargramostim (100 µg) was given subcutaneously every two weeks for a total of 4 doses. Patients that survived 6 months without disease progression or regimen-limiting toxicity received additional booster doses of vaccine every three months until tumor progression. Use of the study drug is registered with the FDA under IND #14674. All investigations were performed under a clinical therapeutic protocol approved by the Institutional Review Board at RPCI and in accordance with an assurance filed with the U.S. Department of Health and Human Services. Informed consent was obtained from each subject prior to treatment.

Patient Characteristics and Treatment

Study population consisted of patients 18 years of age or older who had histological proof of recurrent or progressive glioblastoma or anaplastic glioma, following failure of standard therapy. Karnofsky performance status (KPS)≥70, HLA-A*02 or HLA-A*03 haplotype and documented survivin expression by tumor cells were all required for entry. In addition, absence of infection, white blood cell count≥3,000/mm$^3$, platelets≥100,000/mm$^3$, hemoglobin≥10.0 g/dL, and normal renal and hepatic function were required. Patients were required to use contraceptive methods during and after treatment. Cranial surgery (repeat resection) was permitted prior to entry, but vaccine could not be administered before the 14th post-operative day. Enrolled patients received at least 4 doses (one every two weeks) of the vaccine to be evaluable for immunological and clinical response. All patients were followed for T cell and antibody responses and with brain MM scans to assess tumor response and progression.

Immunohistochemistry

Detection of survivin in surgical tumor specimens was performed with rabbit monoclonal survivin antibody clone EP119 (ready-to-use, Bio SB, Santa Barbara, Calif.), and IDH-1 (R132H) was detected with mouse anti-human IDH-1 R132H monoclonal antibody clone H09 (1:50, Dianova, Germany) using a Dako Omnis autostainer (Dako North America, Inc. Carpinteria, Calif.). The percentage of cells expressing survivin was determined by manual counting. IDH-1 mutational status was determined by the presence or absence of cytoplasmic staining.

Exosome Isolation from Blood

Patient serum samples (n=8) were collected and stored within 3 hours at −80° C. Blood samples were collected from normal (non-cancer) healthy control individuals (n=3). Exosomes were isolated from thawed serum by differential ultracentrifugation as previously described with some modifications (Théry et al, 2006). Serum (200 µl) was spun by ultracentrifuge at 10,000×g for 80 minutes at 4° C. in 11×34 polycarbonate tubes (Beckman Coulter Inc., Fullerton, Calif.). Supernatant was collected and spun in an ultracentrifuge at 100,000×g for 80 minutes at 4° C. using a TLA 100.2 rotor (Beckman Coulter Inc., Fullerton, Calif.). The supernatant was discarded and exosome pellets were resuspended in 100 µl sterile phosphate buffered saline (PBS).

Electron Microscope Imaging of Exosomes

Exosomes were isolated from 300 µl of patient sera as described above and resuspended in 50 µl PBS, to which 50 µl of 4% paraformaldehyde was added. Samples were loaded onto Formvar-carbon grids (Electron Microscopy Sciences, Hatfield, Pa.) as described in Théry et al, 2006 with modification: grids were incubated on droplets of exosomes for 40 minutes at room temperature, washed once in PBS, and then incubated on droplets of 1% EM-grade glutaraldehyde for 5 minutes. Grids were stained with UranyLess (EMS, Hatfield, Pa.) according to manufacturer instructions. Dried grids were imaged at 80 kV using a JEOL JEM-100CX II Transmission Electron Microscope at the SUNY Buffalo Electron Microscopy Core Facility.

Exosome Labeling and Data Acquisition

Prior to labeling, conjugated antibodies were spun at 10,000×g to remove antibody aggregation as previously described (Erdbrügger et al, 2014). 20 µl of exosomes in PBS were stained with Alexa Fluor 488 GFAP antibody (Cat. No. 644704, BioLegend, San Diego, Calif.), PE anti-human CD9 antibody (Cat. No. 312106, BioLegened, San Diego, Calif.), and DyLight 650 survivin antibody (Cat. No. NB500-238C, Novus Biologicals, Littleton, Colo.) for 30 minutes at 26° C. Data were acquired on an ImageStream®X Imaging Flow Cytometer (AMNIS/Millipore). Fluorescent signals were collected as follows: Alexa Fluor 488 was measured with a 480-560 nm bandpass filter, Phycoerythrin (PE) was measured at 560-595 nm with a bandpass filter, and Allophycocyanin (APC) and Dylight 650 were measured with a 642-745 nm bandpass filter. Side-scatter signals were measured at 785 nm excitation (745-800 nm bandpass). All readings were acquired at 60× using 200 µl of sample at low flow rate collected over five minutes. Data analysis was performed using IDEAS software v6.1. A uniform gating strategy was applied on CD9+ events versus side scatter. Further analysis included GFAP and survivin (SVN) events based on CD9+ gate. In addition to CD9, serum exosomes were confirmed positive for CD63 and CD81 tetraspanin expression (data not shown) and morphological size (FIG. 1D).

Statistical Analysis

Exosomes, within a single patient, were compared as percent increase or decrease in relation to the raw exosome counts measured in the baseline sample. Analysis of statistical significance was performed on raw exosome counts using an unpaired Student's t test. Correlations were assessed using Pearson's correlation coefficient.

Results

Patient Characteristics

Patient characteristics are listed in Table 1. Patients in this study had recurrent malignant glioma (WHO grade III or IV) and had failed standard treatment including surgery, radiation therapy and chemotherapy with temozolomide (TMZ). All had recurrent or progressive disease documented by MRI at the time of entry. Eight of nine patients originally entered in the study received the full complement of 4 prime-boost doses of vaccine and 3 patients received at least 1 additional booster dose following the prime-boost phase of treatment. The details of the survivin vaccine, adverse events and immunologic effects are reported elsewhere [50]. Of the 9 patients entered in this clinical trial, one individual received only 2 doses of vaccine due to early, rapid tumor progression and is excluded from this analysis. All patients had measureable disease on brain MM scans at entry; however, there was a wide range in the volume of abnormal contrast enhancing tissue on T1-weighted scans at baseline.

Survivin and GFAP Expression by Tumor Cells

A diagnosis of either glioblastoma (FIG. 1A) or anaplastic glioma was made by the neuropathology co-investigator (J. Q.) in all cases. Of 8 evaluable patients, all had GFAP (FIG. 1B) and survivin (FIG. 1C) expression in their tumors, as detected by immunohistochemistry (IHC). GFAP expression was both strong and diffuse in all patients' tumors. Visually detectable survivin expression was present in between 1% and 22% of tumor cells (Table 1). There was no association between IDH-1 mutation status and survivin expression (Table 1).

Glioma Patients Show Unique Circulating Populations of CD+/GFAP+/SVN+ Exosomes

Exosomes isolated from patient sera were confirmed by both electron microscopy (FIG. 1D) and flow cytometry. As exosomes characteristically express the tetraspanin proteins on the outside of their membranes (Andreu Z, Yáñez-Mó M. Tetraspanins in Extracellular Vesicle Formation and Function. Frontiers in Immunology. 2014; 5:442. doi:10.3389/fimmu.2014.00442), we utilized flow cytometry (ImageStream, see Methods above) to detect populations of CD9-positive species. Although several different tetraspanins are expressed by exosomes, in our preliminary studies, fluorochrome-conjugated CD9 antibody provided more sensitive detection of isolated exosomes than either CD63 or CD81 antibodies (data not shown). Therefore, CD9 was used as the primary marker of exosome detection in our study. Initially, exosomal content was evaluated in serum from glioma patients and healthy controls. CD9+ exosomes were detected in the serum of all normal healthy control patients (n=3) with a mean of 25,036 events per 200 µl. At baseline evaluation (before vaccination), glioma trial patients had a similar expression of exosomes, with a mean of 22,805 CD9+ events per 200 ul serum. In order to determine whether exosomes specifically originating from brain tissue could be detected, we utilized another marker, Glial fibrillary acidic protein (GFAP), in combination with CD9. GFAP is a molecule that, with a few exceptions, is largely confined to the central nervous system and is commonly overexpressed in gliomas. When analyzed for both CD9− and GFAP-positivity, serum from healthy controls had a mean of 527 CD9+/GFAP+ exosomes per 200 µl, whereas serum from glioma patients showed more than 21 times as many CD9+/GFAP+ events (mean=11,298) at baseline (prior to vaccination). Next we evaluated expression of CD9+/SVN+ exosomes. In contrast to healthy patients, who had no detectable levels of CD9+/SVN+ exosomes, most glioma patients had significant levels of CD9+/SVN+ exosomes in serum (mean=891). Finally, when assessing CD9+/GFAP+/SVN+ events, it was found that control individuals had no detectable events (mean=1), whereas glioma patients had substantial numbers (mean=624).

Figure 2:
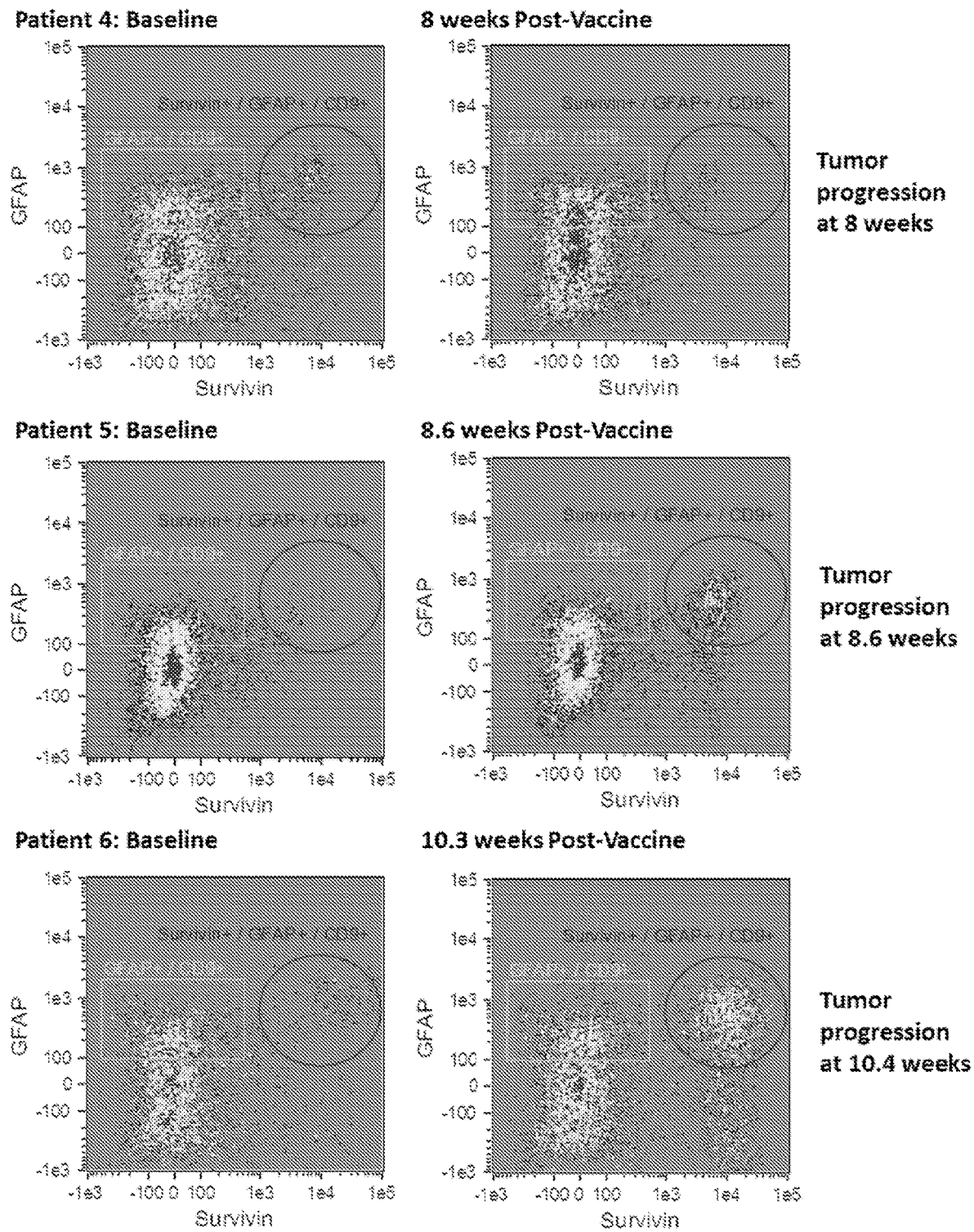
FIG. 2. Representation of CD9+/GFAP+/SVN+ exosomes in patients who progressed early (2-5 months) following initial vaccination by using ImageStream® flow cytometry. (Left column) CD9+/GFAP+/SVN+ exosomes at baseline (prior to first dose of vaccine at study entry), (Right column) CD9+/GFAP+/SVN+ exosomes 8-24 weeks after first dose of vaccine at early tumor progression.
Figure 2:
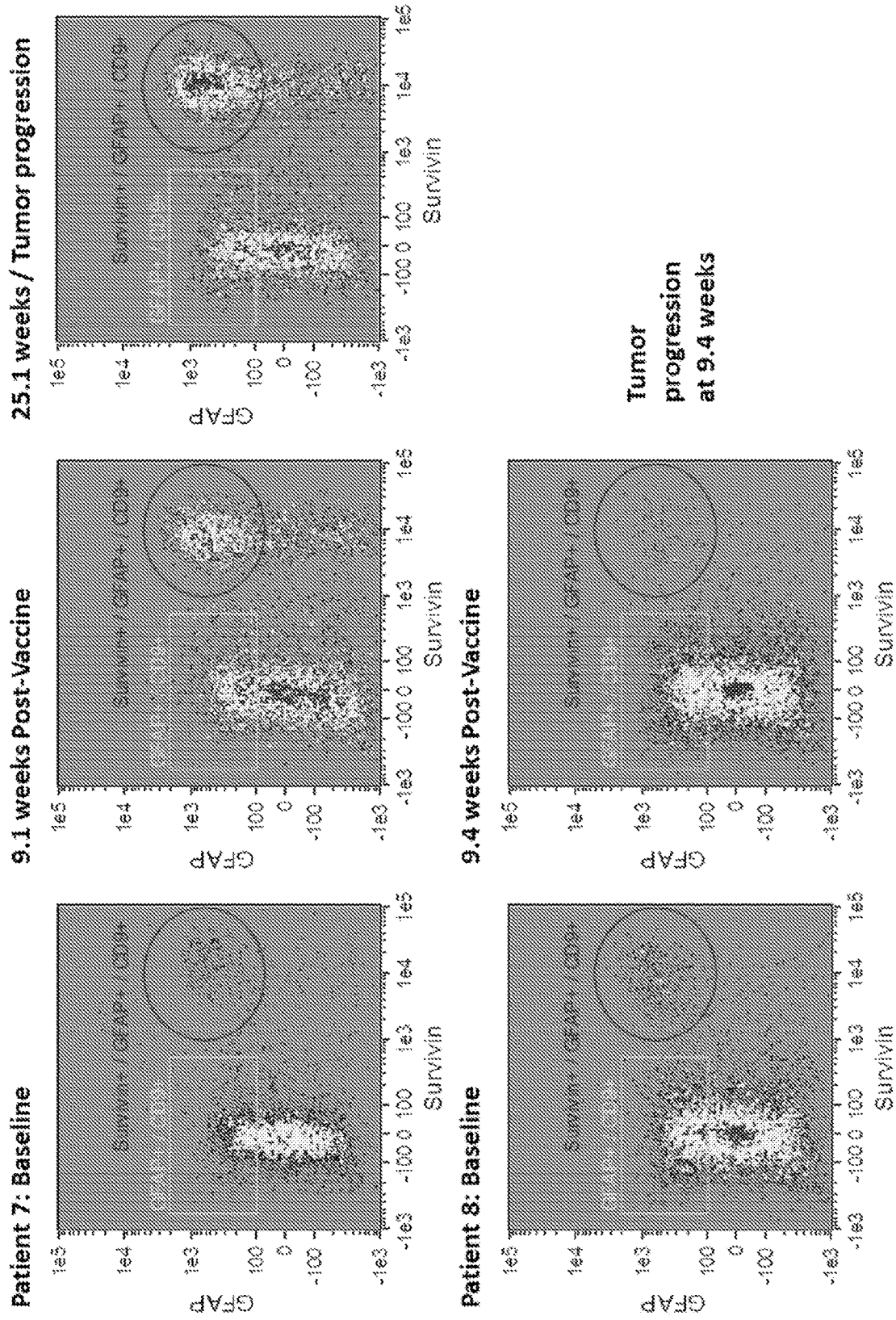
Figure 3:
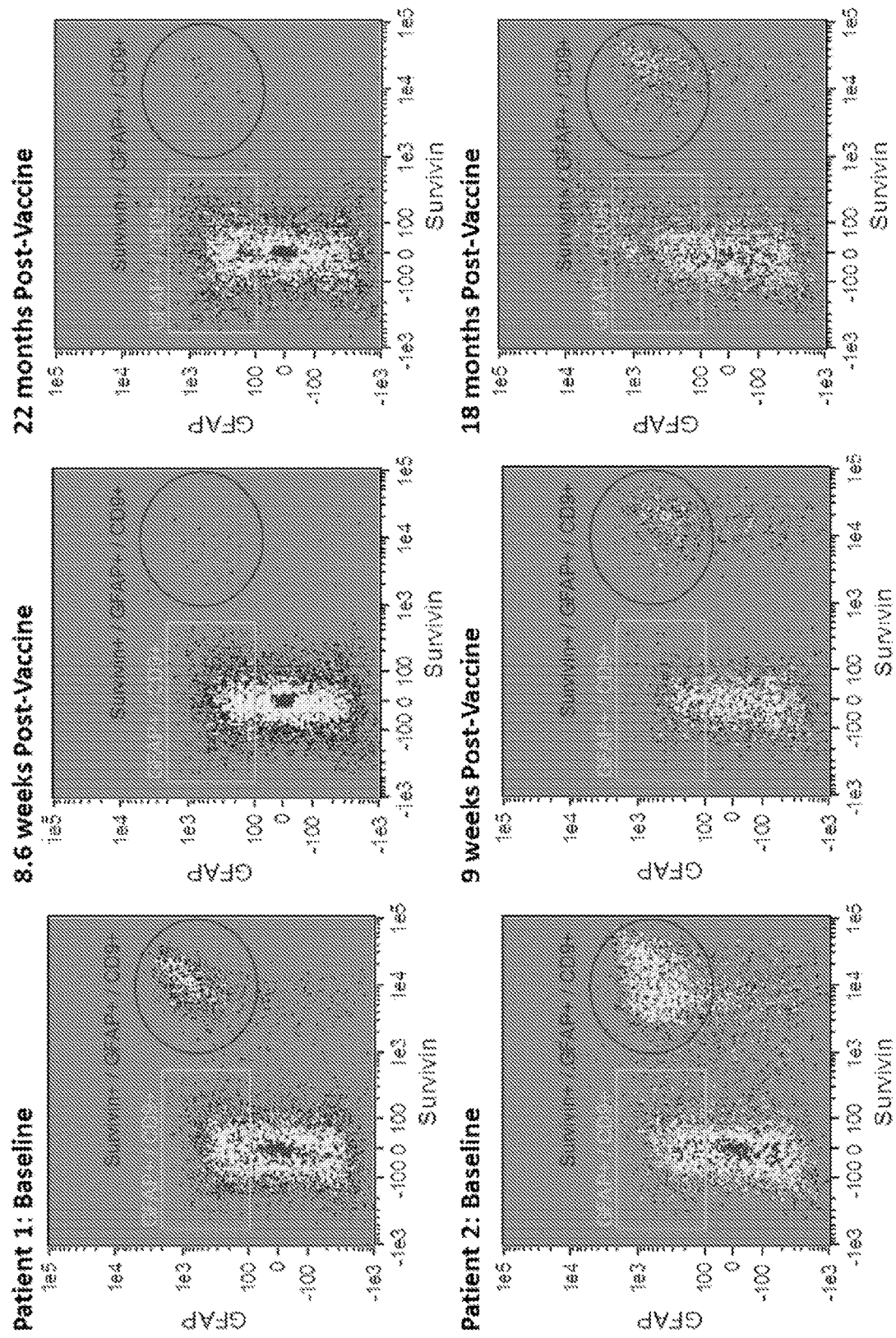
FIG. 3. Representation of CD9+/GFAP+/SVN+ exosomes in patients who had late or no (12-48 months) tumor progression after initial dose of survivin vaccine by using ImageStream® flow cytometry. (Left column) CD9+/GFAP+/SVN+ exosomes at baseline (pre-vaccine); (Middle column) CD9+/GFAP+/SVN+ exosomes 8 weeks after receiving SurVaxM vaccine; (Right column) CD9+/GFAP+/SVN+ exosomes 12-22 months after receiving survivin vaccine. Bottom row demonstrates CD9+/GFAP+/SVN+ exosome events in 3 healthy non-cancer control individuals.
Figure 3:
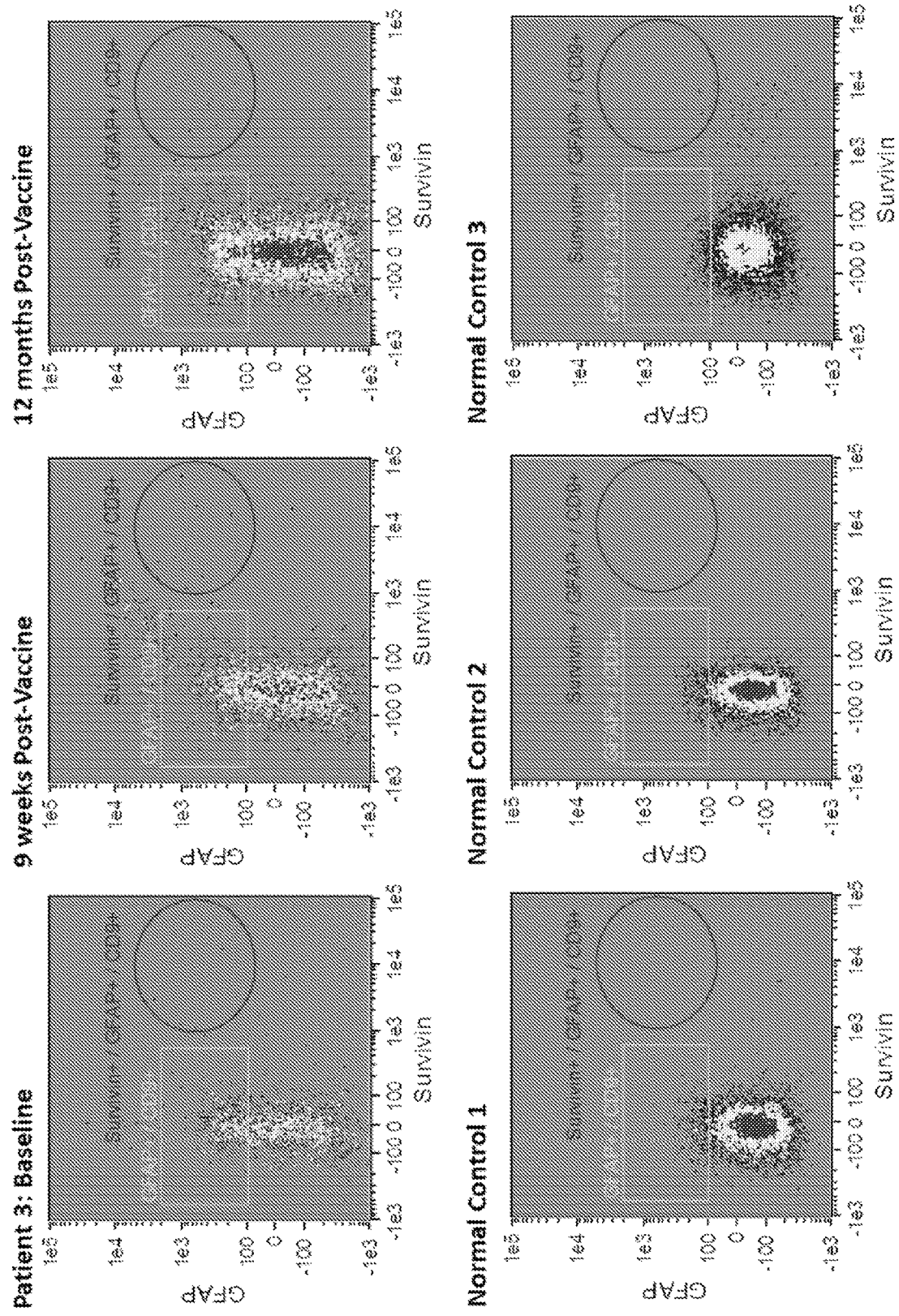

CD9+/GFAP+/SVN+ Exosome Levels Correlate with Longer Time to Progression in Vaccinated Patients To determine whether changes in CD9+/GFAP+/SVN+ exosomes correlated with disease progression, patient serum was evaluated prior to treatment (study entry), 8-10 weeks after initial vaccination, and at the time of MRI-defined tumor progression. Five patients experienced early tumor progression with a mean of 2.8 months (1.9-5.4 months) from study entry, while three patients had either late (20.5-22.5 months) or no tumor progression (no evident disease at 48 months in one patient) (Table 1). Early tumor progression was accompanied by increases in both CD9+/SVN+ and CD9+/GFAP+/SVN+ exosomes (FIG. 2; Table 2), whereas late or absent tumor progression was accompanied by persistent reduction in both CD9+/SVN+ and CD9+/GFAP+/SVN+ exosomes in 2 of 3 patients (FIG. 3; Table 2). One patient with late progression (patient #3) experienced an initial increase in both CD9+/SVN+ and CD9+/GFAP+/SVN+ exosomes at 8 weeks. This individual had low survivin expression (2% of tumor cells) detected by IHC and had exosome counts that were marginally above detectable levels. Interestingly, the patient with no tumor progression (patient #1) experienced a 99% reduction in serum CD9+/GFAP+/SVN+ exosomes, which was sustained over 47 months with vaccine booster doses administered every three months.

Figure 4:
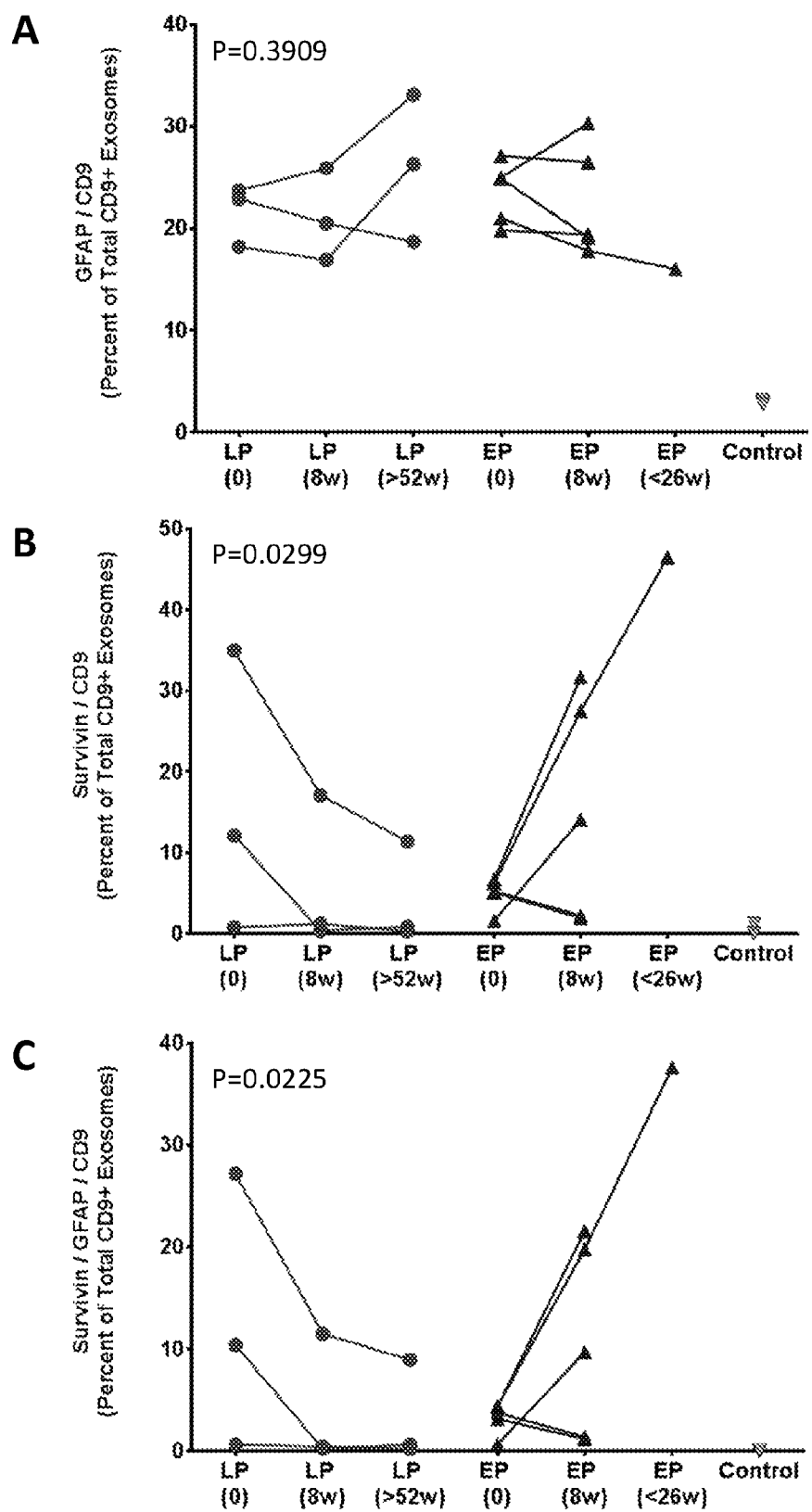
FIG. 4. Comparison of post-vaccination serum exosome events in: (left) at last follow-up at late or no progression, (middle) patients with early tumor progression, and (right) in non-cancer controls (right). Panels display (A) CD9+/GFAP+, (B) CD9+/SVN+, and (C) CD9+/GFAP+/SVN+ (analysis of 200 μl serum).
Figure 5:
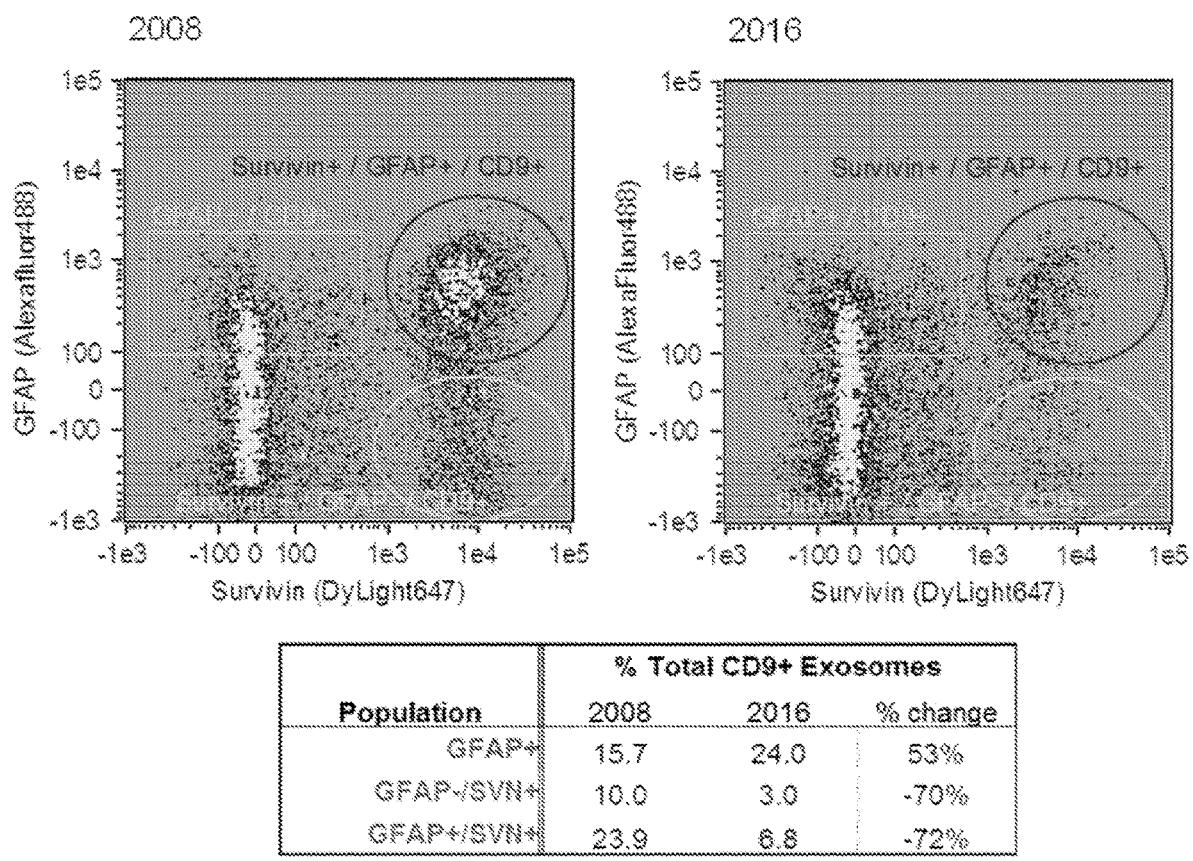
FIG. 5. Representation showing decrease of Survivin/GFAP/CD9 triple labelled exosomes in a long term survivor glioma patient by using ImageStream® flow cytometry.

In order to refine our analysis of glioma-associated exosomes, we quantified changes in exosomes expressing individual markers or combinations of CD9, GFAP and SVN. Patients who progressed early showed increased CD9+/GFAP+ exosome levels in their serum, however this difference was not statistically significant (FIG. 4A; p=0.3909). Exosomes expressing CD9 in combination with either SVN showed statistically significant increases in patients who progressed early, (FIG. 4B; p=0.0299). Combined analysis of all three markers (CD9+/GFAP+/SVN+) also provided statistically significant increases in exosomal content in patients with longer time to progression (FIG. 4D; p=0.0225). The addition of GFAP provided the tissue specificity confidence and sensitivity that exosomes were indeed brain tissue (tumor) derived. We further quantified the number of CD9+/GFAP+/SVN− exosomes found in patients during treatment/progression. The number of CD9+/GFAP+/SVN− exosomes also decreased following survivin vaccination in two of three patients with late/no progression (patients 1 & 2), although not to the same extent as did CD9+/GFAP+/SVN+ exosomes (Table 2). In patients with early progression, CD9+/GFAP+/SVN− events uniformly increased at following the vaccination series.

In this disclosure, we have examined changes in the survivin-containing exosomal content of serum from GMB patients treated with the vaccine SurVaxM. By employing ImageStream flow cytometry technology we were able to analyze multiple markers on individual exosomes, identifying highly specific populations of survivin+ exosomes which co-expressed the brain/tumor marker protein GFAP. The combination of these markers made it possible to differentiate patient exosomes from those of healthy individuals, as levels of CD9+/GFAP+, CD9+/SVN+, and CD9+/GFAP+/SVN+ exosomes were significantly increased in patients. The need for sophisticated approaches in parsing tumor-derived populations of exosomes is underlined by our finding that healthy individuals and GBM patients expressed similar amounts of CD9+ exosomes in their serum. Among patients we identified statistically significant increases in levels of CD9+/GFAP+/SVN+ exosomes in those who progressed early (1.9-5.4 months) compared to those who progressed late (20.5-22.5 months). Our study suggests that SVN+ exosomal content may be altered during immunotherapy treatment (in this case, with SurVaxM). Serum from patients 1 and 2, who experienced the longest progression-free intervals, showed 98-99% decreases in CD9+/GFAP+/SVN+ exosomes after treatment with SurVaxM, and maintained similarly low exosome levels over several months. Interestingly, another patient experienced a detectable increase in CD9+/GFAP+/SVN+ exosomes at 9 weeks following vaccination, 16 weeks prior to the detection of tumor progression by brain MM scan. This may indicate that CD9+/GFAP+/SVN+ exosomes levels can be predictive of relapse. CD9+/GFAP+/SVN+ exosome levels may be used for monitoring disease progression including response to vaccine treatment (such as SurVaxM treatment). Further, rises in CD9+/GFAP+/SVN+ exosomes levels may be used as predictive tools.

The invention has been described through specific embodiments. These embodiments are intended to be illustrative. Routine modifications will be apparent to those skilled in the art, and such modifications are intended to be within the scope of this disclosure.

---

---

The invention claimed is:

1. A method for evaluating the efficacy of a therapy in an individual being treated for glioma comprising: (i) determining a reference circulating level of exosomes that are positive for CD9, a glial marker, and survivin (CD9+/Glial marker+/SVN+ exosomes), (ii) at selected time during therapy, determining whether the level of circulating CD9+/Glial marker+/SVN+ exosomes in the individual is at or below the reference level, said determination indicating that the therapy is efficacious; and (iii) continuing the therapy in an individual having a level of CD9+/Glial marker+/SVN+ exosomes at or below the reference level, or discontinuing or changing the therapy in an individual having a level of CD9+/Glial marker+/SVN+ exosomes above the reference level.

2. The method of claim 1, wherein the glial marker is glial fibrillary acidic protein.

3. The method of claim 1, wherein the circulating levels of CD9+/Glial marker+/SVN+ exosomes are determined in a biological fluid.

4. The method of claim 3, further comprising the step of obtaining an exosome rich fraction from the biological fluid prior to determining levels of CD9+/Glial marker+/SVN+ exosomes.

5. The method of claim 1, wherein the level of CD9+/Glial marker+/SVN+ exosomes in the biological fluid is determined by a combination of high resolution imaging and flow cytometry.

6. The method of claim 3, wherein the biological fluid is blood, plasma or serum.

7. The method of claim 1, wherein the therapy is one or more of surgery, radiation, and chemotherapy.

8. The method of claim 1, wherein the therapy is surgery followed by immunotherapy comprising administration of a composition comprising a peptide of SEQ ID NO:1.

9. The method of claim 8, wherein step (i) is carried out after surgical resection of a tumor but prior to administration of immunotherapy.

10. A method of treating an individual with a glioma comprising:
   i) surgically removing the glioma;
   ii) measuring a level of CD9+/Glial marker+/SVN+ exosomes;
   iii) administering to the individual a composition comprising a peptide of SEQ ID NO:1;
   iv) at different times after administration of said composition, determining the level of circulating CD9+/Glial marker+/SVN+ exosomes in the individual; and
   v) if the circulating levels of CD9+/Glial marker+/SVN+ exosomes are found to be above the reference level, then subjecting the individual to further treatment.

11. The method of claim 10, wherein the further treatment is surgery, radiation, chemotherapy, or immune therapy.

12. The method of claim 10, wherein the glial marker is glial fibrillary acidic protein.

* * * * *